United States Patent
Hoevel et al.

Patent Number: 5,836,444
Date of Patent: *Nov. 17, 1998

[54] POUCH FOR ORTHODONTIC APPLIANCE

[75] Inventors: Kenneth E. Hoevel, Monrovia; Bruce E. Chester, Irvine, both of Calif.; Gregory D. Crowe, Louisville, Ky.

[73] Assignee: Minnesota Mining & Manufacturing Co., St. Paul, Minn.

[*] Notice: The term of this patent shall not extend beyond the expiration date of Pat. No. 5,655,653.

[21] Appl. No.: 840,952

[22] Filed: Apr. 21, 1997

Related U.S. Application Data

[62] Division of Ser. No. 501,186, Jul. 11, 1995, Pat. No. 5,655,653.

[51] Int. Cl.[6] ............................. A61B 19/02; B65D 65/36
[52] U.S. Cl. ......................... 206/63.5; 206/469; 383/205
[58] Field of Search ................. 206/484, 466, 206/459.5, 63.5, 461, 469; 383/203, 205

[56] References Cited

U.S. PATENT DOCUMENTS

| | | |
|---|---|---|
| 2,931,493 | 4/1960 | Pfohl . |
| 2,931,494 | 4/1960 | Pfohl . |
| 2,965,225 | 12/1960 | Zoller et al. ............................. 206/63.3 |
| 2,993,589 | 7/1961 | Zoller et al. ......................... 383/209 X |
| 3,111,220 | 11/1963 | Bostrom . |
| 3,144,343 | 8/1964 | Fritsche . |
| 3,186,628 | 6/1965 | Rhode ..................................... 383/209 |
| 3,246,747 | 4/1966 | Blish . |
| 3,255,869 | 6/1966 | Keller ................................. 383/209 X |
| 3,276,669 | 10/1966 | Vilutis . |
| 3,315,802 | 4/1967 | Lonholdt et al. ....................... 206/63.3 |
| 3,429,432 | 2/1969 | Cabernoch et al. .................... 383/209 |
| 3,547,257 | 12/1970 | Armentrout .............................. 206/439 |
| 3,559,799 | 2/1971 | Kramer et al. ........................... 206/469 |
| 3,625,351 | 12/1971 | Eisenberg ............................. 383/207 X |
| 4,055,672 | 10/1977 | Hirsch et al. . |
| 4,108,309 | 8/1978 | Bronner ............................... 383/209 X |
| 4,116,338 | 9/1978 | Weichselbaum .................... 383/209 X |
| 4,166,535 | 9/1979 | Gilling ................................. 206/469 X |
| 4,251,712 | 2/1981 | Parr . |
| 4,266,666 | 5/1981 | Kuchenbeeker ........................ 206/461 |
| 4,355,721 | 10/1982 | Knott, II et al. . |
| 4,466,534 | 8/1984 | Dunn . |
| 4,506,789 | 3/1985 | Dluqosz .............................. 206/484 X |
| 4,537,305 | 8/1985 | Takanashi . |
| 4,572,377 | 2/1986 | Beckett . |
| 4,712,572 | 12/1987 | Hovel, III . |
| 4,785,940 | 11/1988 | Wilson . |
| 4,848,066 | 7/1989 | Luhman . |
| 4,852,728 | 8/1989 | Court . |
| 4,881,644 | 11/1989 | Norquest et al. . |
| 4,917,929 | 4/1990 | Heinecke . |
| 4,923,309 | 5/1990 | VanErden .................................... 383/5 |
| 4,977,003 | 12/1990 | Brown et al. . |
| 4,979,611 | 12/1990 | Bolliger et al. . |
| 4,981,213 | 1/1991 | Dillon .................................... 206/469 |
| 5,322,077 | 6/1994 | Corella . |
| 5,328,363 | 7/1994 | Chester et al. . |
| 5,348,154 | 9/1994 | Jacobs et al. . |
| 5,655,653 | 8/1997 | Chester .................................. 206/63.5 |

FOREIGN PATENT DOCUMENTS

| | | |
|---|---|---|
| 0 753 288 A3 | 4/1997 | European Pat. Off. . |
| 0 750 887 A3 | 5/1997 | European Pat. Off. . |
| 3733524 A | 10/1987 | Germany . |

*Primary Examiner*—Bryon P. Gehman
*Attorney, Agent, or Firm*—James D. Christoff

[57] ABSTRACT

A pouch especially adapted for packaging small articles such as orthodontic appliances includes a pair of sheets that are joined together. In one embodiment, one sheet of the pouch extends beyond the other sheet in order to provide additional space for text or other information. In another embodiment, the pouch includes a tamper evident indicator and a recloseable section so that the pouch can be reused. In another embodiment, a line of perforations extends across the pouch and across an orthodontic archwire packaged in the pouch, so that the archwire can be grasped with a tool when the package is opened along the perforations without directly contacting the user.

8 Claims, 4 Drawing Sheets

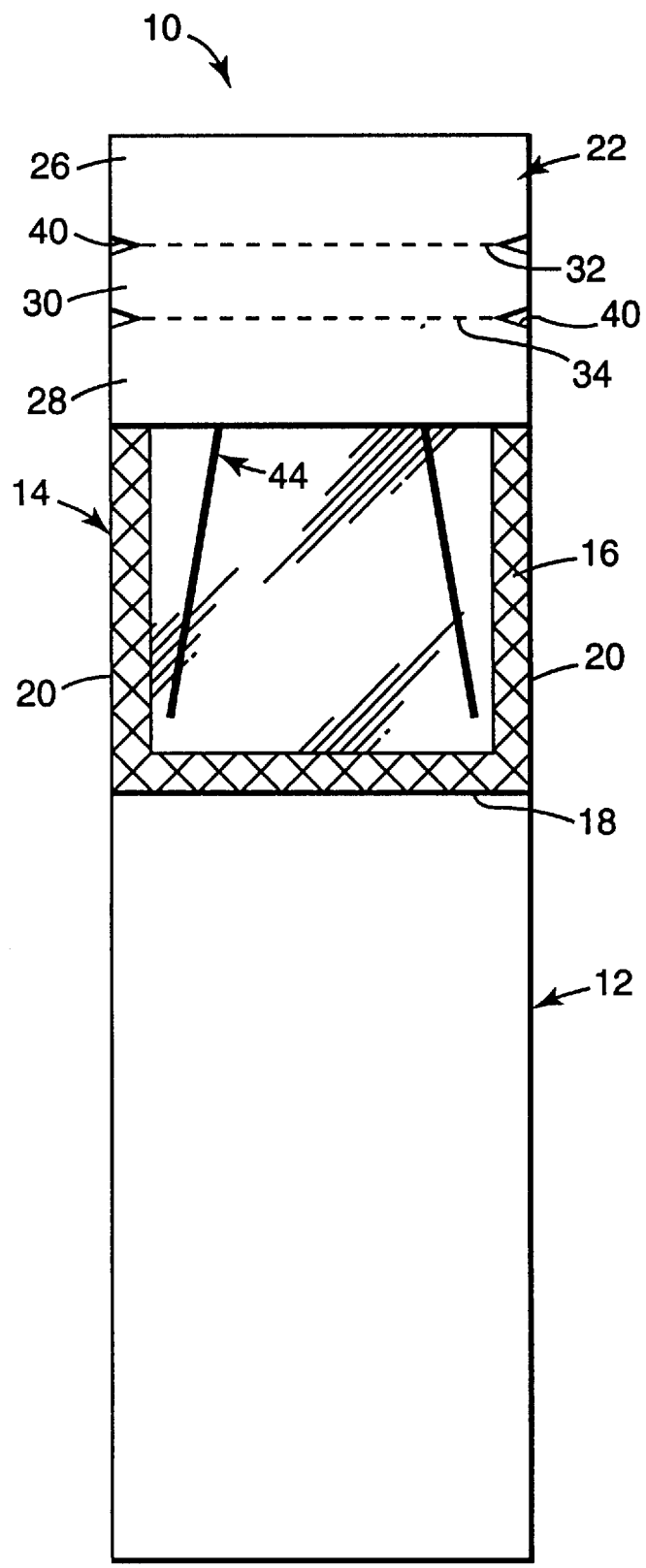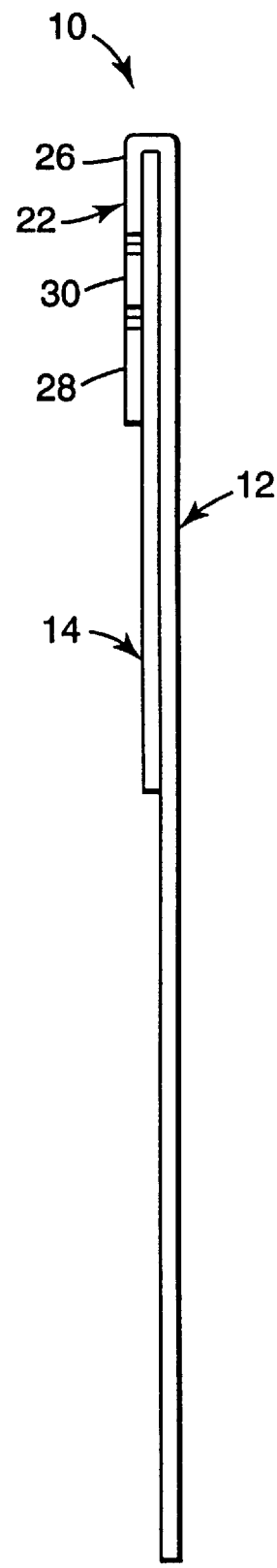
FIG. 2     FIG. 3

POUCH FOR ORTHODONTIC APPLIANCE

This is a division of application Ser. No. 08/501,186 filed Jul. 11, 1995, now U.S. Pat. No. 5,655,653.

BACKGROUND OF THE INVENTION

1. Field of the Invention

This invention relates to a pouch especially adapted for storing and displaying small articles such as orthodontic appliances. The invention also concerns a packaged article that includes an orthodontic archwire received in a pouch that is especially convenient to open.

2. Description of the Related Art

Orthodontic treatment often involves the use of a variety of small articles commonly called appliances. For example, one type of orthodontic treatment may include the use of small, slotted appliances known as brackets that are fixed to teeth of the patient's upper and lower dental arch. Another appliance known as an archwire is then placed in the slots of each bracket, and serves as a track to guide movement of the teeth to orthodontically correct positions. In addition, appliances known as buccal tubes are often fixed to the molar teeth and serve as an anchor for ends of the archwire.

A wide selection of different appliances are available to the orthodontist and vary in size, shape and material of construction. For example, brackets may be made of stainless steel, plastic or ceramic and may have a slot with a particular configuration that is especially adapted for use with an archwire having a matching cross-sectional configuration. Moreover, different brackets are often selected for use with different teeth. For example, the slot of each bracket may be oriented in a particular direction to facilitate moving the associated tooth to an orthodontically correct position. The overall shape of the bracket may have a particular configuration to avoid impinging other brackets or teeth, and the width of the bracket may be narrower or wider in accordance with the width of the underlying tooth.

A variety of different archwires are also available and a number of different archwires are typically retained on hand by the orthodontist for use when needed. Archwires are available in varying overall sizes to match the size of the patient's upper or lower dental arch. In addition, archwires may have a round, square or rectangular cross-sectional configuration and may be of different sizes in accordance with the orthodontist's preferred treatment technique.

Many other small appliances are also often retained on hand by the orthodontist for use when desired. Examples of such other appliances include buccal tubes, lingual sheaths, buttons, auxiliary archwires, springs, ligatures and force modules. Maintaining an inventory represents a certain expense by necessity, but is advantageous in that a particular appliance may be readily selected and used by the orthodontist for a particular treatment when needed without waiting for the appliance to be shipped to the orthodontist by the manufacturer.

A number of different packages have been used in the past to store, display and dispense orthodontic appliances. Orthodontic appliances are relatively small and often a number of identical appliances are packaged in a single container. Unfortunately, such packaging may provide an opportunity for appliances in the container to be contaminated whenever the container is opened to remove a single appliance.

As a consequence, there has been increased interest in recent years in unit-of-use packaging, wherein a single appliance is packaged in its own container. In some instances, the appliance and the interior of the container have been sterilized by the manufacturer. Other containers are not sterilized by the manufacturer, but are adapted to be placed in an autoclave by the orthodontist to sterilize the container and its contents.

Many orthodontic appliances have been packaged in pouches. Some pouches are reduced-size versions of well-known plastic sandwich bags that have a zipper-type closure on one end. Such pouches sometimes have a printed label adhered by a pressure sensitive adhesive to its outside surface. Moreover, some pouches have a printed insert that is placed inside the pouch next to the appliance.

Other orthodontic pouches are made by cutting two panels or sheets of equal size, and then adhering or otherwise joining the sheets together along their periphery to enclose an appliance between the sheets. One sheet is made of flexible clear plastic material to facilitate viewing of the packaged appliance. The other sheet is often made of flexible paper or other material having a printable surface, so that the manufacturer's name, a description of the packaged appliance and other information such as instructions or lot numbers may be provided directly on the pouch.

While the various pouches and other packages used to contain orthodontic appliances and other devices in the past have been satisfactory in some respects, there are some problems with such packages and pouches that remain to be overcome. For one thing, smaller pouches often do not provide a sufficient space for printing a large quantity of text, such as when the package or pouch is distributed in several countries and the text needs to be printed in several languages. In addition, some packages and pouches are somewhat difficult and cumbersome to open.

There is a need in the art for an improved pouch that overcomes the problems noted above.

SUMMARY OF THE INVENTION

One aspect of the present invention is directed toward a pouch that comprises a first sheet made of a flexible material and having at least one printable surface for printing text, and a second sheet extending over the first sheet to define a product-receiving receptacle therebetween. The second sheet is made of a clear plastic material and is fixed to the first sheet at least partially along a path circumscribing the receptacle. The first sheet extends beyond the second sheet a sufficient distance to present an additional area for printing text.

Another aspect of the present invention is directed toward a pouch that comprises a first sheet having at least one printable surface, and a second sheet having a first side and a second side facing away from the first side. At least one of the sheets is made of a clear plastic material. The first sheet extends over the first side of the second sheet and defines a product-receiving receptacle therebetween. The first side of the second sheet is fixed to the first sheet at least partially along a path that circumscribes the receptacle. The first sheet also includes a folded-over portion that extends along at least part of the second side. The folded-over portion includes a first section fixed to the second side, a second section repositionably fixed to the second side and a third section located between the first section and the second section. The folded-over portion includes a first line of weakness extending between the first section and the third section and a second line of weakness extending between the second section and the third section. The first line of weakness and the second line of weakness enable the third section to be torn away from the first section and the second section before the pouch is opened, whereby a tamper evident indicator is provided.

The present invention is also directed to a packaged article that comprises a first sheet, a second sheet extending over the first sheet and an orthodontic archwire located between the first sheet and the second sheet. The second sheet is fixed to the first sheet at least partially along a path circumscribing the archwire. The first sheet and the second sheet each include a line of weakness extending across the archwire such that when the first sheet and the second sheet are torn along the lines of weakness, a first part of the archwire is exposed for grasping while a second part of the archwire remains between the first sheet and the second sheet.

These and other aspects of the invention are described in more detail in the following paragraphs and in the accompanying drawings.

BRIEF DESCRIPTION OF THE DRAWINGS

FIG. 2 is a view somewhat similar to FIG. 1 except that an orthodontic archwire has been placed in the pouch and the pouch has been closed and sealed by the manufacturer;

FIG. 3 is a side elevational view of the pouch shown in FIG. 2;

DETAILED DESCRIPTION OF THE PREFERRED EMBODIMENTS

Figure 1:
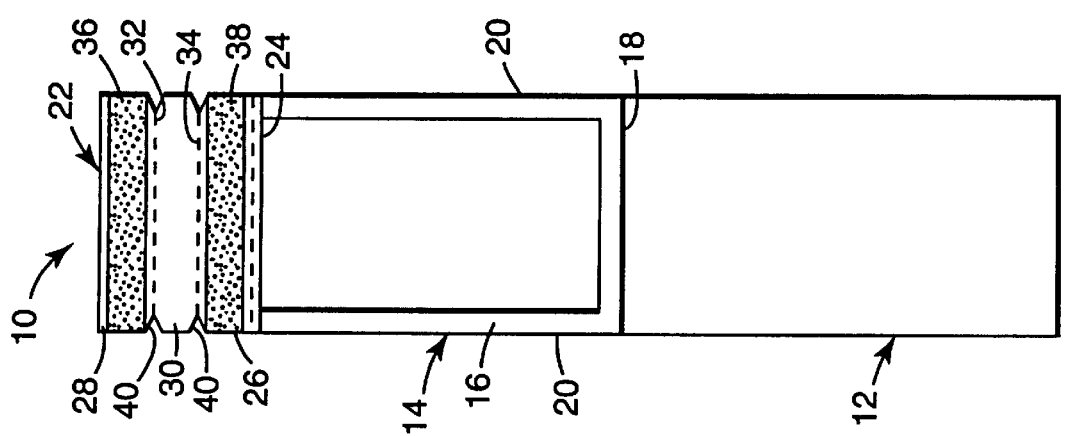
FIG. 1 is a front elevational view of a pouch according to one embodiment of the invention and as it appears before an article such as an orthodontic appliance is placed in the pouch by the manufacturer.

A pouch constructed according to one embodiment of the invention is illustrated in FIGS. 1–3 and is broadly designated by the numeral 10. The pouch 10 includes a first sheet 12 and a second sheet 14. Both sheets 12, 14 have a flat configuration, and their thicknesses are exaggerated in FIG. 3 to facilitate explanation.

The first sheet 12 has at least one printable surface. Preferably, the first sheet 12 is flexible and has printable surfaces on both of its sides. Suitable materials for the first sheet 12 include 28 lb./ream (13 kg/ream) uncoated ledger bond paper stock, although other types of paper and also printable plastic films may instead be employed.

The second sheet 14 extends over the first sheet 12 to define a product-receiving receptacle therebetween. The second sheet 14 is preferably made of a flexible material that is transparent so that the product in the receptacle can be readily viewed. Suitable materials for the second sheet 14 include clear plastic films such as 1 mil (0.025 mm) thick clear polyethylene.

The second sheet 14 has a first side that is fixed to the first sheet 12 partially along a path 16 that circumscribes the product-receiving receptacle. More specifically, the path 16 extends along a bottom edge 18 of the second sheet 14 and along two side edges 20 of the second sheet 14. The path 16 has a generally U-shaped configuration. The first side of the second sheet 14 is fixed to the first sheet 12 along the path 16 by any of a number of suitable methods such as heat sealing, induction sealing, cold sealing, welding or by using an adhesive (such as a pressure sensitive adhesive) or a cohesive.

As shown in the drawings, the first sheet 12 extends past the bottom edge 18 of the second sheet 14 a sufficient distance to provide significant additional area available for printing text. Such additional area is useful, for example, for printing product descriptions, lot numbers, manufacturer's identification, instructions or other information in different languages, a particularly useful feature when the pouch 10 is to be sold in a number of countries. If desired, the bottom portion of the pouch 10 below the bottom edge 18 can be folded upwardly over itself to conserve space in shipping or storage, and may if desired be folded near the bottom edge 18 and extend across the second side of the second sheet 14 to help minimize the size of the pouch 10.

The first sheet 12 includes an upper portion 22 that originally extends beyond an upper edge 24 (FIG. 1) of the second sheet 14. During manufacture of the pouch 10, the upper portion 22 is folded over the upper edge 24 and extends along the second side of the second sheet 14. The upper, folded-over portion 22 includes a first section 26, a second section 28 and a third section 30 that is located between the sections 26, 28. Each of the sections 26, 28, 30 has a generally rectangular configuration.

The folded-over portion 22 includes a first line of weakness 32 that extends between the first section 26 and the third section 30. The folded-over portion 22 also includes a second line of weakness 34 that extends between the second section 28 and the third section 30. The lines of weakness 32, 34 are preferably parallel to the upper edge 24 and the bottom edge 18 of the second sheet 14.

The lines of weakness 32, 34 are comprised of perforations and are optionally made by using a perfwheel. A suitable perforation pattern includes perforations that are about 0.09 in. (2.4 mm) long, with each perforation being spaced from the next adjacent perforation a distance of 0.03 in. (0.8 mm). Other perforation patterns as well as other types of lines of weakness (such as continuous or discontinuous indentation lines) may also be employed.

A length of double sided adhesive 36 (see FIG. 1) extends longitudinally along the first section 26 and is affixed to the second side of the second sheet 14 when the upper portion 22 is folded over in the manner illustrated in FIGS. 2 and 3. Suitable materials for the adhesive 36 include sections of polyester film that are coated on both sides with a high tack pressure sensitive adhesive. An example of a suitable adhesive 36 is no. 9458 double-sided tape from 3M Company.

A repositionably adhesive 38 (see FIG. 1) releasably fixes the second section 28 of the first sheet 12 to the second side of the second sheet 14. Suitable materials for the adhesive 38 include sections of polyester film that are coated on one side with a high tack pressure sensitive adhesive and on the opposite side with a low tack repositionable adhesive. An example of a suitable adhesive 38 is no. 9425 double-sided tape from 3M Company. The high tack side of the adhesive tape is placed against the second section 28, so that the low tack side of the adhesive is in a position to contact the second side of the second sheet 14 once the portion 22 is folded over in the manner shown in FIGS. 2 and 3.

The lines of weakness 32, 34 enable the third section 30 to be torn away from the first section 26 and the second section 28 before the pouch 10 is opened in order to provide a tamper evident indicator. Once the third section 30 is separated from the sections 26, 28, the second section 28 can be lifted from the second sheet 14 and unfolded in order to gain access to the contents of the pouch 10. The first section 26 remains in place since it is fixed to the second sheet 14 by the high tack adhesive 36.

Advantageously, the contents within the pouch 10 (such as the orthodontic archwire 44 shown in FIG. 2) can be removed without touching the repositionable adhesive 38. The repositionable adhesive 38 enables the pouch 10 to be re-used as a storage container in instances where more than one article or appliance is sold with the pouch 10, or in instances where the article or appliance has not been used and is returned to storage. The tamper evident indicator assures the customer that the article or appliance has not been used or otherwise contaminated by a third party, and if left unbroken can also facilitate return of the article or appliance to the manufacturer for credit if desired.

Preferably, the folded-over portion 22 includes notches 40 that are located on each end of each line of weakness 32, 34. The notches 40 facilitate grasping of the edge of the third section 30 when it is desired to open the pouch 10. The notches 40 also help promote tearing of the first sheet 12 along the lines of weakness 32, 34 as the third section 30 is lifted away from the underlying portion of the second sheet 14.

Figure 4:
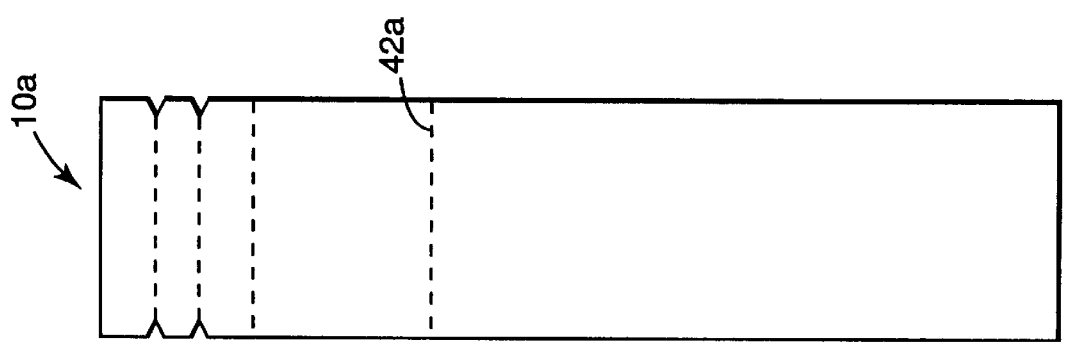
FIG. 4 is a rear elevational view of a pouch somewhat similar to that shown in FIG. 1 but according to another embodiment of the invention.

FIG. 4 is a rear view of a pouch 10a according to another embodiment of the invention. The pouch 10a includes a first sheet 12a and a second sheet (not shown) that are identical to the first sheet 12 and the second sheet 14 described above except for the differences noted in the following paragraphs.

The pouch 10a includes a third line of weakness 42a which extends from one side of the pouch 10a to the other. The line of weakness 42a is preferably a line of perforations that extends through both the first sheet 12a and the underlying second sheet in an area across the product-receiving receptacle between the sheets. As an example, the third line of weakness 42a is made of perforations that are approximately 0.04 in. (1 mm) in length separated by spaces of approximately 0.04 in. (1 mm).

The third line of weakness 42a provides an alternative method for opening the pouch 10a in instances where the pouch 10a will not be reused. The third line of weakness 42a is advantageous in that the pouch 10a can be quickly opened by simply grasping portions of the pouch 10a on opposite sides of the line of weakness 42a and pulling such portions apart from each other. If desired, notches similar to notches 40 (see FIGS. 1–2) may be provided at each end of the line of weakness 42a to further enhance rupturing of the pouch 10a along the line of weakness 42a.

Figure 5:
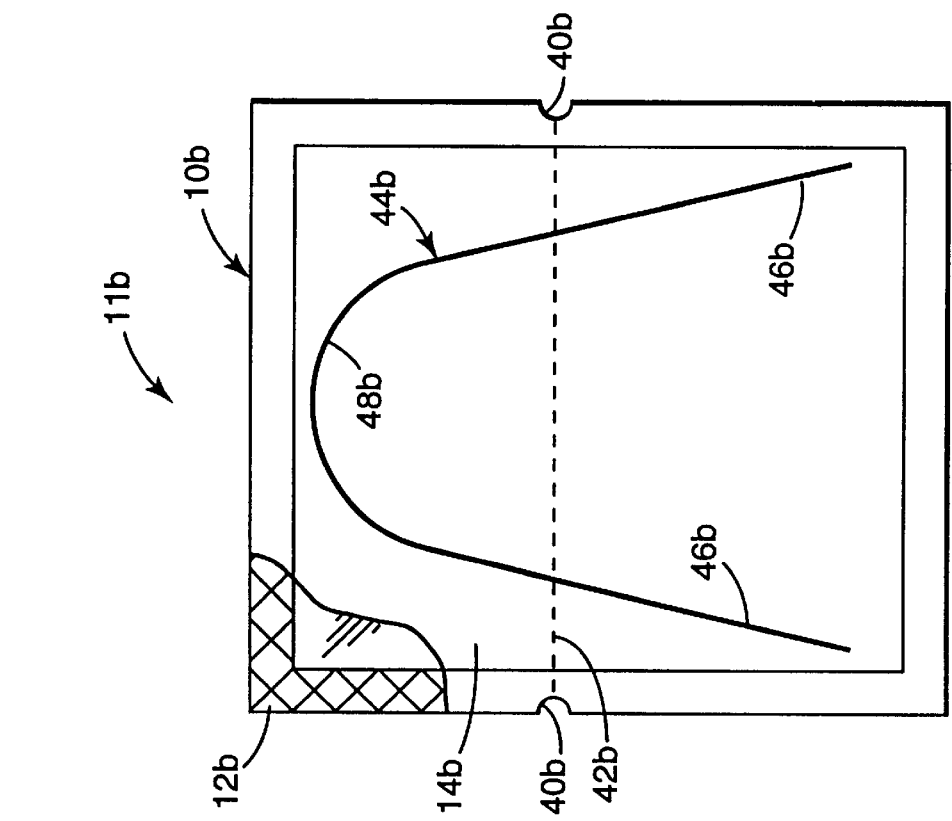
FIG. 5 is a front elevational view according to yet another embodiment of the invention wherein a packaged article includes an orthodontic archwire and a pouch.

FIG. 5 is an illustration of a packaged article 11b according to another embodiment of the invention. The packaged article 11b includes a pouch 10b and a orthodontic archwire 44b that is received in a product-receiving receptacle of the pouch 10b.

The pouch 10b includes a first sheet 12b and a second sheet 14b that extends over the first sheet 12b. Preferably, the first sheet 12b is made of a flexible material having a printable surface such as the materials described above in connection with sheet 12. The second sheet 14b is preferably transparent and is made of a flexible material similar to the materials described above in connection with the sheet 14.

As shown in FIG. 5, the sheets 12b, 14b have identical heights and widths. Further, the second sheet 14b is fixed to the first sheet 12b along a path that extends around the archwire 44b and completely circumscribes the archwire 44b once manufacture is complete. The sheets 12b, 14b are preferably fixed together by heat sealing, although other means are also possible such as pressure sensitive adhesives, cohesives, induction sealing, welding, cold sealing or the like.

A line of weakness 42b extends across both of the sheets 12b, 14b from one edge to another. Preferably, the line of weakness 42b is comprised of a series of perforations that extend through both of the sheets 12b, 14b. Suitable perforations include perforations that are 0.04 in. (1 mm) in length and spaced apart a distance of 0.04 in. (1 mm) distance from each other. The sheets 12b, 14b have notches 40b located at each end of the line of weakness 42b.

The archwire 44b illustrated in FIG. 5 is typical of many orthodontic archwires, and includes a pair of spaced apart legs 46b that are integrally interconnected to each other by a curved bight portion 48b. Preferably, the line of weakness 42b is positioned to extend across both legs 46b as is illustrated in FIG. 5.

The pouch 10b is opened by grasping portions of the pouch 10b on each side of the line of weakness 42b, and pulling the portions apart until the portions are separated. If the user firmly grasps the lower portion of the pouch 10b over one or both of the legs 46b and loosely grasps the upper portion of the pouch 10b or grasps only a corner section of such upper portion, the upper portion of the pouch 10b is easily lifted away from the archwire 44b to expose the bight portion 48b. The user can then grasp the bight portion 48b with a tweezers (or by hand if preferred) and simply pull the archwire 44b out of the remaining portion of the pouch 10b without touching the legs 46b.

As can be appreciatted by reference to FIG. 5, the space between the legs 46b provides a location for grasping the packaged article 11b within the confines of the archwire 44b without pressing directly on the archwire 44b.

The location of the line of weakness 42b is an advantage in that the pouch 10b can be opened and the bight portion 48b exposed without coming into contact with the user's hands. Tweezers or other tools may then be used to remove the archwire 48b from the pouch 10b without contacting the skin of the user. In this manner, the likelihood of contaminating the archwire 44b is significantly reduced.

Figure 6:
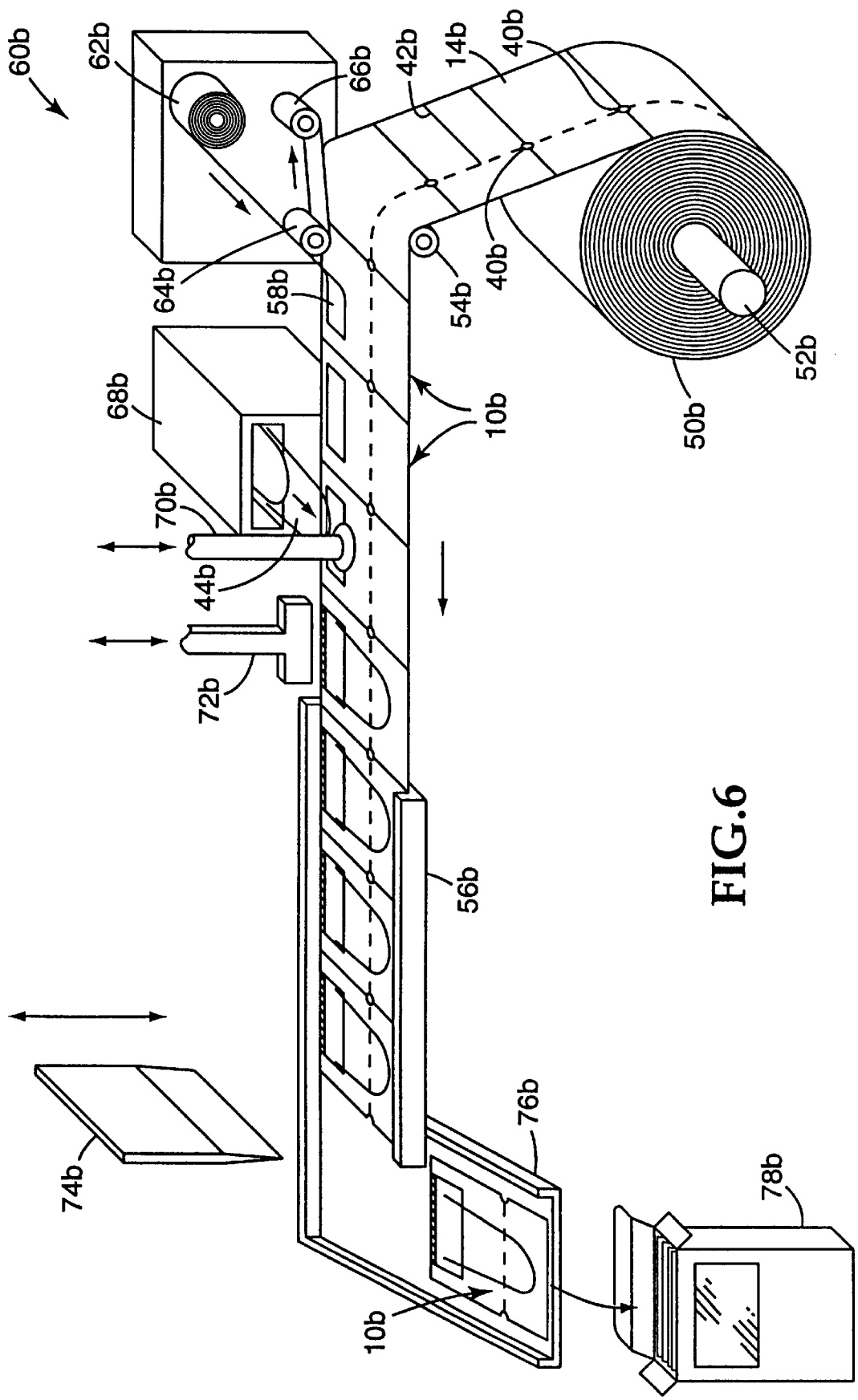
FIG. 6 is a reduced perspective view in partially schematic form illustrating one method of assembly of the packaged article delpicted in FIG. 5.

FIG. 6 is an illustration of one method of manufacturing the pouch 10b, although such method could also be adapted to manufacture pouches 10 or 10a as well. In FIG. 6, a roll of material 50b is received on an unwind spindle 52b that is optionally connected to a drive motor for selective rotation. The roll of material 50b is comprised of an initially joined-together series of first and second sheets 12b, 14b that have been previously heat sealed along the top and two sides of the path that is shown in FIG. 5. As can be further appreciated by reference to FIG. 6, the roll of material 50b includes the line of weakness 42b and notches 40b that are positioned along the sides of adjacent pouches 10b.

As the roll of material 50b is unwound, the material passes over an idler roller 54b and toward a U-shaped guide track 56b made of a material such as, for example, DELRIN brand acetal resin, from DuPont, although other materials could also be employed. Although not shown, a transport drive that includes a series of upstanding pegs is located beneath a central slot of the track 56b. The pegs are connected to a chain and sprocket drive or walking beam drive, and pass through the holes between adjacent pouches 10b that are formed by the notches 40b. When the transport drive is activated, the pegs move along the length of the track 56b to advance the material in the direction indicated by the arrow.

Once the material passes by the idler roller 54b, a label 58b is optionally applied to the front of each pouch 10b by a combination on-line printer and labeler 60b. The combination printer and labeler 60b includes a roll 62b of color-coded blank label stock, and the label stock passes over a guide roller 64b located immediately above the advancing pouch material.

The underside of the label stock has a pressure sensitive adhesive and a release liner initially covering the pressure sensitive adhesive. As the label stock passes over the guide roller 64b, the release liner is separated from the label stock and is wound on a take-up spool 66b. The printer mechanism is not shown, but is optionally an ink-jet printer which can add information in addition to any information printed on the printable first sheet of the pouch 10b.

As the pouch material advances, each pouch 10b moves to a position directly adjacent an archwire inserter station 68b. At that time, advancement of the pouch material is interrupted and a tube 70b that is optionally rigid) descends toward the pouch 10b. The lower end of the tube 70b includes a resilient rubber cup, and the tube 70b is connected to a source of negative air pressure.

As the tube 70b contacts the pouch 10b, the negative air pressure is applied to the tube 70b in order to releasably fix the second sheet 14b of the pouch 10b to the tube 70b. Next, the tube 70b is raised a small distance in order to separate the unsealed edge portions of the pouch sheets 12b, 14b. The archwire inserter station 68b is then activated to slide an archwire such as archwire 44b into the product receiving receptacle between the sheets 12b, 14b of the pouch 10b.

As an alternative to the negative air pressure, a puff of air could instead be employed to separate the sheets 12b, 14b. Moreover, it may be desired in some instances to intermittently apply a source of negative air pressure to the first sheet 12b of the pouch 10b as negative air pressure is applied to the second sheet 14b in order to facilitate separation of the sheets.

Once the archwire is placed in the pouch 10b, the negative air pressure is relieved and the transport drive is activated to advance the filled pouch 10b. The pouch 10b then advances to a heat sealing station that includes a heated bar 72b. Movement of the pouch 10b is then interrupted, and the heated bar 72b descends to heat seal the remaining portion of the path circumscribing the product receiving receptacle and the archwire 44b therein. Preferably, heat sealing of one pouch 10b is done during the time that the next adjacent pouch 10b behind is receiving an archwire.

As the pouch 10b advances and passes by the end of the track 56b, a knife 74b descends to cut apart the pouch 10b from remaining pouch material. The separated pouch 10b then slides down a chute 76b under the influence of gravity until it falls to a receiving station or alternatively directly into a carton 78b. Optionally, an inspection station can be located over the chute 76b for manual inspection. Alternatively, devices such as video cameras could provide for automated inspection of such items including satisfactory heat seals, label placement and presence of archwire.

Figure 7:
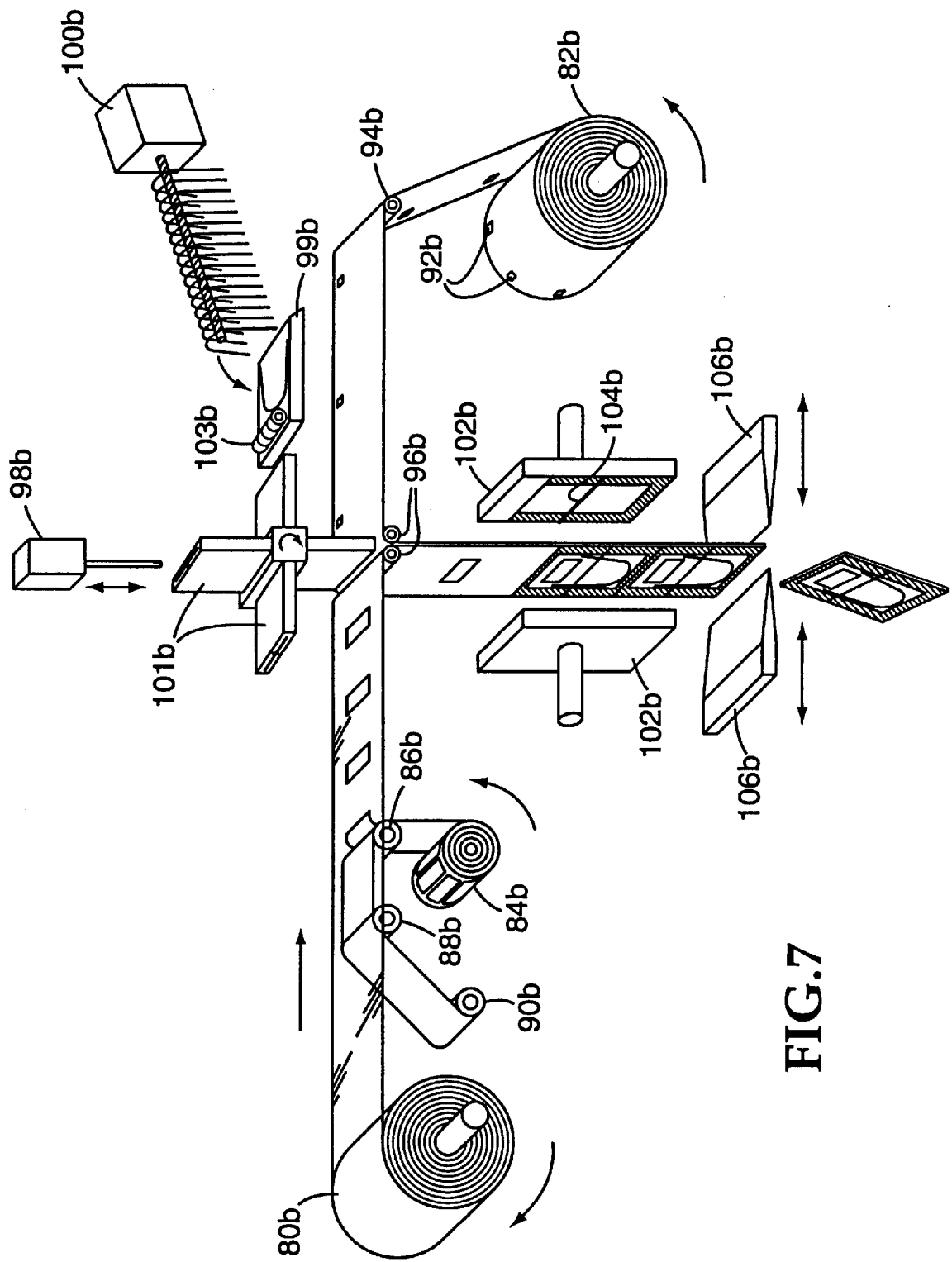
FIG. 7 is a view somewhat similar to FIG. 6 except showing another method of assembly of the packaged article illustrated in Fig. 5.

Another method of manufacturing the pouch 10b is schematically shown in FIG. 7 and includes the use of a roll 80b of clear plastic material and a roll 82b of pre-printed paper stock. Both of the rolls 80b, 82b are received on respective spindles.

The plastic material from the roll 80b passes over an on-line printer and labeler that includes a roll 84b of color-coded blank label stock. As the label stock advances, a printer (not shown) such as an ink-jet printer applies suitable information to the face of each label. The label stock then ascends to an idler roller 86b where the label is applied to one side of the plastic material.

A release liner of the label stock passes over the idler roller 86b. The release liner is wound on a take-up spool 90b.

The paper stock includes a series of printed registration eyespots 92b that are detected by a sensor (not shown) to insure that each pouch seal path or pattern is placed in registration with the text printed on the paper stock. The paper stock passes over a idler roller 94b. Both the paper stock and the film stock pass through a nip between two pairs of spaced apart idler rollers 96b. The rollers 96b are located immediately beneath an archwire inserter mechanism 98b having a vertically reciprocal plunger.

The paper stock and film stock descend toward a space between a pair of pouch forming dies 102b, one of which is heated. At an appropriate time, movement of the paper and film stock is interrupted and the dies 102b move horizontally toward each other to contact the paper and film stock and create a U-shaped heat seal pattern. As shown in FIG. 7, one of the dies 102b includes a perforation knife 104b that creates a line of weakness such as the line of weakness 42b illustrated in FIG. 5. Subsequently, the dies 102b move away from each other to retracted positions.

An archwire screw feed conveyor 100b includes a feed screw shaft that is received in a cylindrical bore of a horizontally-extending support. The bottom and sides of the screw shaft are surrounded by the support, while an upper portion of the screw shaft is exposed. An archwire is received in each space between adjacent threads of the exposed portion of the screw shaft, and as the shaft rotates the archwires advance toward a horizontal table 99b. Optionally, a guide plate extends along and below one side of the support to keep the advancing archwires in an aligned, upright orientation.

When each archwire arrives at the end of the screw shaft, the archwire falls onto the table 99b. Next, a pusher bar (not shown) pushes the fallen archwire into a rectangular cavity of one of four paddles 101b. An optional set of roller guides 103b is located over the end of the table 99b and helps maintain the archwire (and particularly the legs of the archwire) in a horizontal plane aligned with the rectangular cavity as the archwire is pushed into the slot.

The four paddles 101b are fixed to a single hub that is rotatable about a horizontal axis. After the pusher bar retracts from the rectangular cavity, the hub rotates 90° to bring the paddle loaded with the archwire into a vertical orientation directly over the nip between the rolls 96b. The cavity has a configuration such that the legs of the archwire resiliently engage sides of the cavity so that the archwire remains in the cavity as the hub rotates to move the loaded paddle 101b toward a vertical orientation.

Next, the plunger of the inserter mechanism 98b descends through a central passage in the uppermost paddle 101b, through a passage in the hub and also through a central hole in the lowermost paddle 101b that is aligned with the other two passages. The plunger engages the middle of the bight portion of the archwire, and then continues its descent in order to push the archwire into a position between the plastic film stock and the paper film stock and within the confines of the heat seal pattern. Optionally, a slender, vertically oriented guide is located in the space between adjacent pairs of the idler rollers 96b. The guide extends both above and below the rollers 96b and serves to keep the paper and plastic film stock slightly apart from each other. The guide has an internal passageway through which the archwire passes as the plunger descends.

Although not shown in the drawing, a pair of rubber drive wheels located below the dies 102b engage opposite edge portions of one side of the laminated paper and film stock. A pair of steel follower wheels engage edge portions of the opposite side of the laminated paper and film stock. The rubber drive wheels are powered by an electric steppermotor.

Once the archwire is placed within the partially closed pouch, the rubber drive wheels resume advancement of the plastic and paper film stock. The paper and film stocks and the archwire descend toward a pair of cutoff scissors or knives 106b. Advancement of the film and paper stocks is then interrupted and the knives cut through the middle of the lower, horizontal portion of the U-shaped heat seal pattern, such that the severed pouch 10b is sealed on all four edges. Preferably, the knives 106b move toward each other to cut the pouch 10b at the same time that the dies 102b move toward each other to heat seal the film and paper stocks for a subsequent pouch.

Rotation of the rubber drive wheels, movement of the dies 102b, and operation of the cutoff knives 106b, the archwire screw feed conveyor 100b, the archwire inserter mechanism 98b and the paddles 101b are controlled by a programmable controller. Preferably, a sensor is coupled to the controller for detecting the presence of an archwire on the table 99b, and another sensor is connected to the controller for confirming that the plunger of the inserter mechanism 98b is raised before rotation of the hub and the four paddles 101b. In addition, the sensor (mentioned previously) that detects the registration eyespots is connected to the controller. Optionally, another sensor could be provided to confirm that an archwire is received in the pouch before the cutoff knives 106b sever the pouch.

While the methods of manufacturing the invention as described in FIGS. 6 and 7 have been discussed specifically in connection with the pouch 10b, it should be understood in this regard that such methods may also be adapted for use with manufacturing other pouches of the invention as well. Moreover, those skilled in the art can recognize that a number of other variations and modifications to the pouches and to the methods of manufacture as described above can be carried out without departing from the spirit of the invention. Accordingly, the invention should not be deemed limited by the detailed description of the presently preferred embodiments set out above, but only by a fair scope of the claims that follow along with their equivalents.

We claim:

1. A pouch comprising:

a first sheet made of a flexible material and having at least one printable surface for printing text; and a second sheet extending over said first sheet and defining a product-receiving receptacle therebetween, said second sheet being made of a clear plastic material, said second sheet being fixed to said first sheet at least partially along a path circumscribing said receptacle, said first sheet extending beyond said second sheet a sufficient distance to permit an additional area for printing text, wherein said first sheet includes a folded-over portion, wherein said folded-over portion is fixed to said second sheet, wherein said folded-over portion includes a first section fixed to said second sheet, a second section repositionably fixed to said second sheet and a third section located between said first section and said second section, and wherein said folded-over portion also includes a first line of weakness extending between said first section and said third section and a second line of weakness extending between said second section and said third section, said first line of weakness and said second line of weakness enabling said third section to be torn away from said first section and said second section before said pouch is opened, whereby a tamper evident indicator is provided.

2. The pouch of claim 1, wherein said folded-over portion is repositionably fixed to said second sheet.

3. The pouch of claim 1, wherein at least one of said lines of weakness comprises perforations.

4. The pouch of claim 1, wherein said folded-over portion includes printed text.

5. The pouch of claim 1, including an orthodontic appliance received in said receptacle.

6. The pouch of claim 5, wherein said orthodontic appliance is selected from the group consisting of an archwire, a bracket, a buccal tube, a button, a cleat and a spring.

7. A pouch comprising:

a first sheet made of a flexible material and having at least one printable surface for printing text;

a second sheet extending over said first sheet and defining a product-receiving receptacle therebetween, said second sheet being made of a clear plastic material, said second sheet being fixed to said first sheet at least partially long a path circumscribing said receptacle, said first sheet extending beyond said said second sheet a sufficient distance to permit an additional area for printing text; and an orthodontic archwire received in said receptacle between said first sheet and said second sheet, said archwire being generally U-shaped and having a first leg, a second leg spaced from said first leg and a middle portion interconnecting said first leg and said second leg and wherein said first sheet and said second sheet each include a line of weakness extending across said first leg and said second leg such that when said first sheet and said second sheet are torn along said lines of weakness, said middle portion of said archwire is exposed for grasping while a portion of said first leg and said second leg of said archwire remains between said first sheet and said second sheet and whereby the space between said first leg and said second leg provides a location for grasping said article within the confines of said archwire without pressing directly on said archwire.

8. The pouch of claim 7, wherein at least one of said lines of weakness comprises perforations.

* * * * *